(12) United States Patent
Lo et al.

(10) Patent No.: US 6,664,056 B2
(45) Date of Patent: Dec. 16, 2003

(54) NON-INVASIVE PRENATAL MONITORING

(75) Inventors: Yuk Ming Dennis Lo, Kowloon (HK); Lit Man Poon, Tsuen Wan, N.T. (HK)

(73) Assignee: The Chinese University of Hong Kong, Hong Kong (HK)

( * ) Notice: Subject to any disclaimer, the term of this patent is extended or adjusted under 35 U.S.C. 154(b) by 0 days.

(21) Appl. No.: 09/876,005

(22) Filed: Jun. 6, 2001

(65) Prior Publication Data

US 2002/0045176 A1 Apr. 18, 2002

Related U.S. Application Data

(60) Provisional application No. 60/241,417, filed on Oct. 17, 2000.

(51) Int. Cl.[7] .............................. C12Q 1/68; C12P 19/34
(52) U.S. Cl. ...................... 435/6; 435/91.2; 435/91.21; 435/91.51
(58) Field of Search .................... 435/6, 91.2, 91.21

(56) References Cited

FOREIGN PATENT DOCUMENTS

| WO | WO 97/35589 | 10/1997 |
|----|-------------|---------|
| WO | WO 98/39474 | 9/1998  |

OTHER PUBLICATIONS

Amicucci, Paola, et al., "Prenatal Diagnosis of Myotonic Dystrophy Using Fetal DNA Obtained from Maternal Plasma," *Clinical Chemistry* (2000) vol. 46, No. (2):301–302.

Chiu, Rossa W.K., et al., "Effects of Blood–Processing Protocols on Fetal and Total DNA Quantification in Maternal Plasma," *Clinical Chemistry* (2001) vol. 47, No. (9):1607–1613.

Costa, Jean–Marc, et al., "First–Trimester Fetal Sex Determination in Maternal Serum Using Real–Time PCR," *Prenatal Diagnosis* (2001) vol. 21:1070–1074.

(List continued on next page.)

*Primary Examiner*—Carla J. Myers
(74) *Attorney, Agent, or Firm*—Townsend and Townsend Crew LLP

(57) ABSTRACT

Embodiments of the present invention are directed to the detection of fetal or maternal RNA in a blood sample from a pregnant subject, and may involve subjecting the sample to a test for fetal or maternal analysis indicative of a fetal or maternal condition or characteristics. For instance, the RNA analysis may involve the assessment of the gene expression pattern of an unborn fetus by analyzing a blood sample from the mother. The prenatal monitoring technology allows, for the first time, the detection of genes which are expressed by the fetus, just by analysis of a sample of maternal blood. In specific embodiments, the prenatal monitoring technology is based on the discovery of circulating RNA of fetal origin in the plasma of pregnant women. In general, the detection method performed on a maternal serum or plasma sample from a pregnant female comprises detecting the presence of RNA of fetal or maternal original in the sample.

7 Claims, 2 Drawing Sheets

OTHER PUBLICATIONS

Faas, B.H.W., et al., "Detection of Fetal RHD–Specific Sequences in Maternal Plasma," *The Lancet* (Oct. 10, 1998) vol. 352:1196.

Lo, Y.M. Dennis, et al., "Quantitative Analysis of Fetal DNA in Maternal Plasma and Serum: Implications for Noninvasive Prenatal Diagnosis," *Am. J. Hum. Genet.* (1998) vol. 62:768–775.

Lo, Y.M. Dennis, et al., "Increased Fetal DNA Concentrations in the Plasma of Pregnant Women Carrying Fetuses with Trisomy 21," *Clinical Chemistry* (1999) vol. 45, No. (10) pp: 1747–1751.

Kopreski et al. Clinical Cancer Research. Aug. 1999. 5: 1961–1965.*

Kamm et al. Clinical Chemistry. 1972. 18: 519–522.*

Kjems et al. Acta Oncologica. 1993. 32: 371–378.*

Al–Mufti, Raghad, et al., "Detection of Fetal Messenger Ribonucleic Acid in Maternal Blood to Determine Fetal Rh.D. Status as a Strategy for Non–Invasive Prenatal Diagnosis," *American Journal of Obstetrics and Gynecology* (Jul. 1998) vol. 179, No. (1 ):pp. 210–214.

Cunningham, Joan, et al., "Non–Invasive RNA–Based Determination of Fetal Rhesus D Type: A Prospective Study Based on 96 Pregnancies," *British Journal of Obstetrics and Gynaecology* (Oct. 1999) vol. 106:pp. 1023–1028.

Hamlington, Jeanette, et al., "Prenatal Detection of Rhesus D Genotype," *The Lancet* (Feb. 22, 1993) vol. 349:p. 540.

Kopreski, Michael S., et al., "Detection of Tumor Messenger RNA in the Serum of Patients with Malignant Melanoma," *Clinical Cancer Research* (Aug. 1999) vol. 5:pp. 1961–1965.

Lo, YM Dennis, et al., "Presence of Fetal DNA in Maternal Plasma and Serum," *The Lancet* (1997) vol. 350:pp. 485–487.

Lo, Y.M. Dennis, et al., "Prenatal Diagnosis of Fetal Rh.D. Status by Molecular Analysis of Maternal Plasma," *The New England Journal of Medicine* (Dec. 10, 1998) vol. 339:pp. 1734–1738.

Lo, Kwok–Wai, et al., "Analysis of Cell–Free Epstein–Barr Virus–Associated RNA in the Plasma of Patients with Nasopharyngeal Carcinoma," *Clinical Chemistry* (1999) vol. 45, No. (8):1292–1294.

Page, N., et al., "The development of a Genetic Profile of Placental Gene Expression During the First Trimester of Pregnancy: A Potential Tool for Identifying Novel Secreted markers," *Fetal Diagn. Ther.* (Jul.–Aug. 2000) vol. 15, No. (4):pp. 237–245.

Taniguchi, Rika, et al., "Trophoblastic Cells Expressing Human Chorionic Gonadotropin Genes in Peripheral Blood of Patients with Trophoblastic Disease," *Life Sciences* (2000) vol. 66, No. (17):pp. 1593–1601.

Tsukamoto, Hiroko, et al., "SSCP Analysis by RT–PCR for the Prenatal Diagnosis of Niemann–Pick Disease Type C," *Prenatal Diagnosis* (2000) vol. 21:pp. 55–57.

Yagel, S., et al., "Trophoblasts Circulating in Maternal Blood as Candidates for Prenatal Genetic Evaluation," *Hum. Reprod.* (1994) vol. 9, No. (6):pp. 1184–1189.

* cited by examiner

NON-INVASIVE PRENATAL MONITORING

This application is related to and claims the benefit of U.S. Provisional Patent Application No. 60/241,417, filed Oct. 17, 2000, the entire disclosure of which is incorporated herein by reference.

BACKGROUND OF THE INVENTION

This invention relates to prenatal detection methods using non-invasive techniques and, more particularly, to the detection of fetal or maternal RNA in a blood sample from a pregnant subject, including the assessment of the gene expression pattern of an unborn fetus by analyzing the blood sample.

We have previously described the detection of circulating fetal DNA in maternal plasma and serum. Y. M. Dennis Lo et al., "Presence of Fetal DNA in Maternal Plasma and Serum," Lancet 1997, 350:485–7. We have demonstrated the use of this technology for non-invasive prenatal diagnosis. Y. M. Dennis Lo et al., "Prenatal Diagnosis of Fetal RhD Status by Molecular Analysis of Maternal Plasma," New England Journal of Medicine 1998, 339:1734–8. The discovery of fetal DNA in maternal plasma has opened up a new horizon on prenatal molecular diagnosis. A number of groups have since shown that fetal genetic traits, such as RhD status and inherited genetic diseases, can be determined from fetal DNA in maternal plasma.

The main limitation of this existing technology is that fetal DNA detection will only allow one to tell the presence and quantity of genetic material of fetal origin in the maternal circulation. It does not give information regarding the gene expression profile of the baby. Gene expression patterns can be expected to be affected by physiological or pathological processes affecting the baby and mother. Such direct monitoring of fetal gene expression is beyond the reach of conventional non-invasive technologies.

SUMMARY OF THE INVENTION

Embodiments of the present invention are directed to the detection of fetal or maternal RNA in a blood sample from a pregnant subject, and may involve subjecting the sample to a test for fetal or maternal analysis indicative of a fetal or maternal condition or characteristics. For instance, the RNA analysis may include the assessment of the gene expression pattern of an unborn fetus by analyzing a blood sample from the mother. The utility of the invention has been demonstrated from the second trimester and the third trimester of pregnancy, and may be used for the diagnosis and monitoring of a wide variety of diseases, including pre-eclampsia and preterm labor.

The new prenatal monitoring technology according to the present invention allows, for the first time, the detection of genes which are expressed by the fetus, just by analysis of a sample of maternal blood. This will become a platform technology upon which a new generation of non-invasive prenatal tests can be built.

The prenatal monitoring technology is based on the discovery of circulating RNA of fetal origin in the plasma of pregnant women. Heretofore, it was not known whether fetal RNA was also present in maternal plasma. Using a two-stepped reverse transcriptase polymerase chain reaction (RT-PCR) assay, we demonstrate the presence of fetal-derived, male-specific mRNA in plasma of pregnant women carrying male fetuses. As described herein, fetal RNA is detected by RT-PCR; but in principle any RNA detection method can be used.

This technology is expected to have application in all cases of pregnancy for monitoring the physiological or pathological status of a fetus. It is further anticipated that in certain scenarios, more than one such monitoring may be desirable or necessary during pregnancy. Thus, the number of potential clients and possibilities of multi-usage is potentially enormous.

In accordance with an aspect of the present invention, a method of performing prenatal monitoring or testing of a blood sample obtained from a pregnant subject comprises removing all or substantially all nucleated and a nucleated cell populations from the blood sample to obtain a remaining material. The remaining material is subjected to a test for fetal or maternal RNA analysis indicative of a fetal or maternal condition or characteristic. The remaining material may comprise plasma or serum.

In accordance with another aspect of the invention, a detection method performed on a maternal serum or plasma sample from a pregnant female comprises detecting the presence of RNA of fetal origin in the sample. The fetal RNA may be amplified to facilitate detecting the presence of RNA of fetal origin in the sample. For instance, the fetal RNA may be converted into complementary DNA by a reverse transcriptase and then detected by a polymerase chain reaction.

In some embodiments, the fetal RNA is detected using a sequence specific probe. The RNA detection may involve detecting the presence of a fetal RNA transcribed from the Y chromosome, or a fetal RNA from a gene or other DNA sequences inherited from either the father or the mother. The RNA may be detected by any one of a physical method, an immunological method, and a biochemical method.

In accordance with another aspect of the present invention, detection method performed on a maternal serum or plasma sample from a pregnant female comprises detecting the presence of RNA of fetal or maternal origin in the sample. The RNA detection may involve detecting the presence of RNA transcribed from genes on chromosome 6. The RNA may be transcribed from the HLA-G gene.

Another aspect of the invention is directed to a method of performing prenatal monitoring or testing. The method comprises providing a maternal blood sample, and separating the sample into a predominantly cellular fraction (fraction 1) and a predominantly non-cellular fraction (fraction 2). The presence of RNA of fetal origin is detected in fraction 2. The method further includes providing a diagnosis based on at least one of the following: presence, quantity, concentration, sequence, and biochemical composition of the detected RNA.

In accordance with another aspect of the present invention, a method of performing a prenatal monitoring or testing on a maternal blood sample comprises obtaining a non-cellular fraction of the maternal blood sample, and performing an RNA analysis for expressed human genes on the fraction.

DESCRIPTION OF THE SPECIFIC EMBODIMENTS

Figure 1:
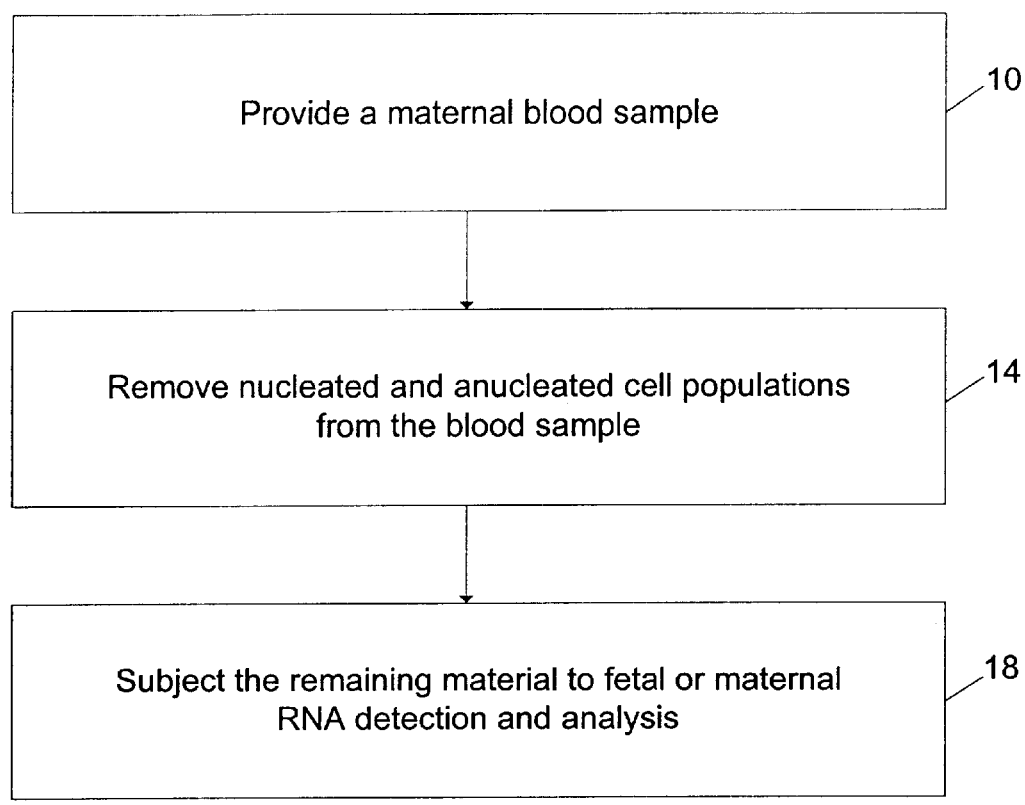
FIG. 1 is a flow diagram illustrating a noninvasive prenatal monitoring method according to an embodiment of the present invention.

As shown in FIG. 1, the method of performing prenatal monitoring or testing of a blood sample obtained from a pregnant subject according to an embodiment of the present invention begins with providing a maternal blood sample (step 10). In step 14, all or substantially all nucleated and a nucleated cell populations are removed from the blood sample. The remaining material is subjected to a test for fetal or maternal RNA analysis indicative of a fetal or maternal condition or characteristic in step 18. The remaining material to be subjected to the RNA analysis may be a cellular matter or a non-cellular matter. In specific embodiments, the remaining material may include plasma or serum. The serum may be obtained, for instance, by allowing clotting in the maternal blood sample.

The maternal serum or plasma sample may be tested to detect the presence of RNA of fetal or maternal origin in the sample. To facilitate the detection of RNA in the sample, the RNA may be amplified. In one example, the fetal or maternal RNA is converted into complementary DNA by reverse transcriptase and then detected by a polymerase chain reaction. Amplifying the fetal or maternal RNA may involve the use of at least one fetal or maternal sequence specific oligonucleotide.

The fetal or maternal RNA may be detected using a sequence specific probe. In one example, detecting the presence of RNA of fetal origin includes detecting the presence of a fetal RNA transcribed from the Y chromosome. More specifically, the fetal RNA may be transcribed from the ZFY gene. The sex of the fetus can be determined from the RNA of fetal origin in the sample. In another example, detecting the presence of RNA of fetal origin in the sample involves detecting the presence of a fetal RNA from a gene or other DNA sequences inherited from the father. In another example, detecting the presence of RNA of fetal or maternal origin in the sample includes detecting the presence of RNA transcribed from genes on chromosome 6. The RNA may be transcribed from the HLA-G gene. The detection of RNA may be performed by any one or more of a physical method, an immunological method, and a biochemical method.

In yet another example, the maternal or fetal RNA detection and analysis is performed on a non-cellular fraction of the maternal blood sample. The non-cellular fraction may be completely or predominantly non-cellular, and is obtained by separation from the completely or predominantly cellular fraction in the blood sample. The RNA analysis may involve a diagnosis based on one or more of the presence, quantity, concentration, sequence, and biochemical composition of the detected RNA. In a specific embodiment, the RNA analysis is performed for expressed human genes on the non-cellular fraction of the sample.

It should be noted that fetal or maternal RNA detection and analysis are still possible even after filtration of the blood sample removing all cellular material to obtain a plasma or serum (i.e., the predominantly cell-free fraction of blood).

The following example is provided to illustrate various features of the present invention, and does not in any way limit the scope of the invention.

In the example, pregnant women attending the Prenatal Diagnosis Unit at the Department of Obstetrics and Gynecology, Prince of Wales Hospital, Hong Kong were recruited with informed consent. The study was approved by the Clinical Research Ethics Committee. Twenty-one and thirty-seven women in early and late pregnancies, respectively, were recruited in this study. The mean gestational ages of the subjects in early and late pregnancies were 16 weeks (range, 11–19 weeks) and 33 weeks (range, 26–40 weeks), respectively. All early pregnancy samples were obtained before any invasive procedure. On the other hand, late pregnancy samples were collected either from women who had invasive procedures in early pregnancy (n=21) or from women who did not have any prenatal invasive procedure (n=16). All plasma samples were harvested within 30 minutes from EDTA blood samples as described previously. See Y. M. Dennis Lo et al., "Presence of Fetal DNA in Maternal Plasma and Serum," Lancet 1997, 350:485–7. Total RNA from plasma samples was isolated with the Trizol LS Reagent (Gibco BRL) as instructed by the manufacturer. In general, RNA isolated from 1 mL of plasma was dissolved in 50 $\mu$L of RNase-free water.

Figure 2:
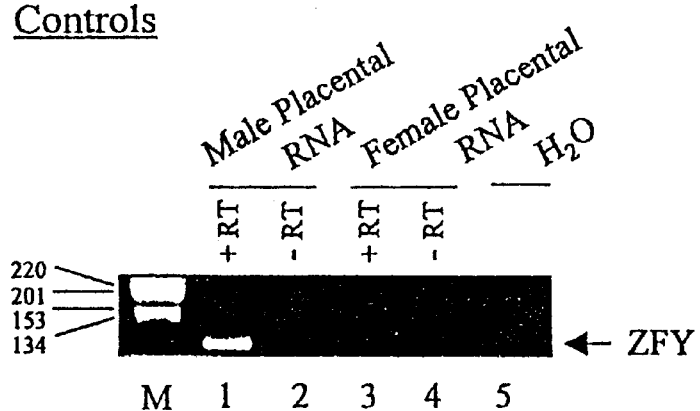
FIG. 2 illustrates the detection of fetal-derived, Y chromosome-specific zinc finger protein (ZFY) mRNA in maternal plasma and for RT-PCR assay for HLA-G mRNA according to an embodiment of the present invention.
Figure 2:
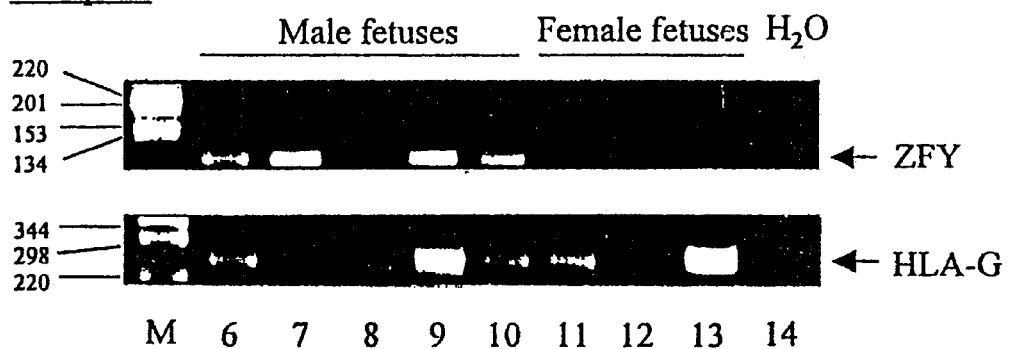

In this study, we chose to detect fetal-derived, Y chromosome-specific zinc finger protein (ZFY) mRNA in maternal plasma. See D. C. Page et al., "The Sex-Determining Region of the Human Y Chromosome Encodes a Finger protein," Cell 1987, 51:1091–104; M. S. Palmer et al., "Comparison of Human ZFY and ZFXTranscripts," Proc. Nat'l Academy Science USA 1990, 87:1681–5. As shown in FIG. 2, RT-PCR products corresponding to ZFY mRNA were observed only when male placental total RNA was used in the RT-PCR assay (FIG. 2, lane 1). By contrast, no positive signal was detected when either RT was omitted (FIG. 2, lane 2) or female placental total RNA was used (FIG. 2, lane 3) in the RT-PCR assays. Among 20 women carrying male fetuses in late pregnancy, ZFY positive signals were detected (FIG. 2, middle panel, lanes 6–10) in 13 plasma samples. Positive signals were observed in 2 out of 9 women carrying male fetuses in early pregnancy. The identity of ZFY mRNA-specific RT-PCR products in the positive cases were confirmed by DNA sequencing (data not shown). By contrast, of 20 women carrying female fetuses either in early (n=12) or in late (n=8) pregnancy, all but one case were negative in the assay (FIG. 2, middle panel, lanes 11–14). The only false-positive case was presumably due to contamination during RNA processing. As a control for the quality of the extracted RNA, we also subjected all samples to an RT-PCR assay for HLA-G mRNA. See T. V. F. Hviid et al., "Co-Dominant Expression of the HLA-G Gene and Various Forms of Alternatively Spliced HLA-G mRNA in Human First Trimester Trophoblast," Hum. Immunol. 1998, 59:87–98. The HLA-G gene is expressed by both fetal (e.g. trophoblast (see id.)) and maternal (e.g. lymphocytes (see M. Kirszenbaum et al., "An Alternatively Spliced Form of HLA-G mRNA in Human Trophoblasts and Evidence for the Presence of HLA-G Transcript in Adult Lymphocytes," Proc. Nat'l Academy Science USA 1994, 91:4209–13)) tissues. As shown in the lower panel of FIG. 2, RT-PCR products specific for HLA-G mRNA were detected in all tested plasma samples, demonstrating the presence of amplifiable RNA in these samples.

Recently, it has been demonstrated that a proportion of maternal plasma fetal DNA circulates in the form of intact fetal cells. See I. J. van Wijk et al., "Detection of Apoptotic Fetal Cells in Plasma of Pregnant Women [Technical Brief], Clin. Chem. 2000, 46:729–31. Thus, theoretically it is possible that the fetal RNA that we detected in the current study could have originated from these 'plasma-derived' cells. To conclusively test if fetal RNA can be detected in cell-free form in maternal circulation, maternal plasma samples were filtered by a 0.2 $\mu$m membrane (Nalgene) and the RNA extracted from these filtered plasma samples was tested by the ZFYRT-PCR assay. Of 9 filtered plasma samples collected from women carrying male fetuses in late pregnancies, positive ZFY mRNA signals were detected in 6 samples (data not shown). These results indicate that at least a portion of fetal RNA in maternal plasma exists in cell-free form.

Our data demonstrate that fetal RNA can be detected in maternal plasma. The detection rate of plasma fetal RNA in early and late pregnancies were 22% and 63%, respectively. The detection rate of fetal RNA in early pregnancy cases was lower than that in late pregnancy cases, suggesting that the concentration of plasma fetal RNA is lower in early pregnancy. This observation is similar to our previous finding that the concentration of fetal DNA in maternal plasma increases with gestation. See Y. M. Dennis Lo et al., "Quantitative Analysis of Fetal DNA in Maternal Plasma and Serum: Implications for Noninvasive Prenatal Diagnosis," Am. J. Hum. Genet 1998, 62:768–75. We also realized that the detection rate of plasma fetal RNA in this study is lower than that of plasma fetal DNA. It is possible that fetal RNA is more susceptible to degradation in maternal blood. As a result, the amount of fetal RNA in plasma is much lower than plasma fetal DNA. This is supported by the fact that Y-specific DNA was detected in all plasma samples from women carrying male fetuses in this study (data not shown). A highly sensitive real-time quantitative RT-PCR assay may be developed to improve the sensitivity of maternal plasma fetal RNA detection.

In conclusion, we have shown, for the first time, that fetal RNA can be detected in maternal plasma, and our data provide a novel way for noninvasive prenatal diagnosis. Plasma fetal DNA analysis can provide data on the presence and concentration of fetal genetic material in the maternal circulation. Plasma fetal RNA analysis, in addition, can provide valuable information regarding the gene expression patterns of fetal tissues. For example, abnormal pregnancies, such as preeclampsia, are often associated with abnormal gene expression patterns in fetal tissues. B. K. Rinehart et al., "Expression of the Placental Cytokines Tumor Necrosis Factor Alpha, Interleukin 1 Beta, and Interleukin 10 is Increased in Preeclampsia," Am. J. Obstet. Gynecol. 1999, 181:915–20. Thus, with the development of further RNA markers, maternal plasma RNA analysis may allow the noninvasive monitoring of fetal gene expression in a multitude of physiological and pathological conditions. It is understood that the term "plasma fetal RNA analysis," as used herein, encompasses analysis of fetal RNA in maternal plasma or maternal serum.

The above-described arrangements of apparatus and methods are merely illustrative of applications of the principles of this invention and many other embodiments and modifications may be made without departing from the spirit and scope of the invention as defined in the claims. For example, while we have demonstrated the feasibility of the concept, further research may elucidate the spectrum of conditions in which this technology can be applied. In addition, further refinement of the technology may be made, for instance, to improve the reliability of the method without departing from the scope of the invention. The scope of the invention should, therefore, be determined not with reference to the above description, but instead should be determined with reference to the appended claims along with their full scope of equivalents.

What is claimed is:

1. A non-invasive method of determining the sex of a human fetus comprising the steps of:
    removing all or substantially all nucleated and anucleated cell populations from a maternal blood sample from the female bearing the fetus to obtain a remaining material;
    detecting in the remaining material, the presence of mRNA transcribed from the ZFY gene; and
    determining the sex of the fetus from the wherein the presence of the mRNA transcribed from the ZFY gene is indicative of a male fetus.

2. The method according to claim 1 wherein the remaining material comprises plasma.

3. The method according to claim 1 wherein the remaining material comprises serum.

4. The method according to claim 1 wherein the step of detecting comprises amplifying the mRNA.

5. The method according to claim 1 wherein the mRNA is converted into complementary DNA by a reverse transcriptase and then detected by a polymerase chain reaction.

6. The method according to claim 1 wherein the mRNA is detected using a sequence specific probe.

7. The method according to claim 1 wherein the mRNA is detected by any one of a physical method, an immunological method, and a biochemical method.

* * * * *